United States Patent [19]
Wells et al.

[11] Patent Number: 5,120,531
[45] Date of Patent: * Jun. 9, 1992

[54] HAIR STYLING CONDITIONERS

[75] Inventors: Robert L. Wells, Cincinnati, Ohio; Bonnie T. King, Alexandria, Ky.; Michael A. Snyder; Donald H. Frey, both of Cincinnati, Ohio

[73] Assignee: The Procter & Gamble Company, Cincinnati, Ohio

[*] Notice: The portion of the term of this patent subsequent to Apr. 14, 2009 has been disclaimed.

[21] Appl. No.: 506,410

[22] Filed: Apr. 6, 1990

[51] Int. Cl.[5] .............................................. A61K 0/75
[52] U.S. Cl. ......................................... 424/70; 424/71
[58] Field of Search ................. 424/70, 71, 78, DIG. 2

[56] References Cited

U.S. PATENT DOCUMENTS

| | | | |
|---|---|---|---|
| 2,816,882 | 12/1957 | Schiller | 526/307.7 |
| 2,834,763 | 5/1958 | Halpern et al. | 526/245 |
| 2,996,471 | 8/1961 | Reiter | 424/47 |
| 3,072,536 | 1/1963 | Pye | 167/85 |
| 3,222,329 | 12/1965 | Grosser et al. | 260/80.5 |
| 3,405,084 | 10/1968 | Bohac | 260/29.6 |
| 3,445,566 | 5/1969 | Skoultchi | 424/17 |
| 3,577,517 | 5/1971 | Kubot et al. | 424/47 |
| 3,743,715 | 7/1973 | Viout et al. | 424/47 |
| 3,810,977 | 5/1974 | Levine | 424/47 |
| 3,907,984 | 9/1975 | Calvert et al. | 424/47 |
| 3,927,199 | 12/1975 | Micchelli | 424/47 |
| 3,936,513 | 2/1976 | Lorenz et al. | 525/379 |
| 4,012,501 | 3/1977 | Farber | 424/47 |
| 4,030,512 | 6/1977 | Papantoniou et al. | 132/7 |
| 4,067,839 | 1/1978 | Schultz | 526/916 |
| 4,151,333 | 4/1979 | Lenke et al. | 526/307.7 |
| 4,165,367 | 8/1979 | Chakrabarti | 424/47 |
| 4,192,861 | 3/1980 | Micchelli | 424/47 |
| 4,196,190 | 4/1980 | Gehman et al. | 424/47 |
| 4,223,009 | 9/1980 | Chakrabarti | 424/47 |
| 4,272,511 | 6/1981 | Papantoniou et al. | 424/47 |
| 4,283,384 | 8/1981 | Jacquet et al. | 424/47 |
| 4,374,825 | 2/1983 | Bolich, Jr. et al. | 424/70 |
| 4,387,090 | 6/1983 | Bolich, Jr. | 424/70 |
| 4,388,436 | 6/1983 | Chen | 524/553 |
| 4,548,990 | 10/1985 | Mueller et al. | 526/320 |
| 4,798,721 | 1/1989 | Yahagi et al. | 424/70 |
| 4,842,852 | 6/1989 | Nowak | 424/71 |
| 4,886,660 | 12/1989 | Patel | 424/70 |
| 4,902,499 | 2/1990 | Bolich, Jr. et al. | 424/47 X |
| 4,963,348 | 10/1990 | Bolich, Jr. et al. | 424/DIG. 2 |

FOREIGN PATENT DOCUMENTS

| | | | |
|---|---|---|---|
| 116207 | 8/1984 | European Pat. Off. | |
| 1195050 | 6/1965 | Fed. Rep. of Germany | 526/307.7 |
| 60-229909 | 11/1985 | Japan | 526/307.7 |
| 60-250015 | 12/1985 | Japan | |
| 0833995 | 5/1981 | U.S.S.R. | 526/307.7 |
| 467402 | 6/1937 | United Kingdom | 526/307.7 |
| 764409 | 12/1956 | United Kingdom | 526/307.7 |
| 2155788 | 10/1985 | United Kingdom | |

OTHER PUBLICATIONS

Technical Leaflet-Luviskol VA grades-Dec. 1984.
Technical Leaflet-Luviskol VAP grades-Feb. 1984.
Encyclopedia of Polymer Science & Engineering, vol. 7, pp. 531–544, John Wiley and Sons, 1987.
Copending Application, Ser. No. 285,137, Torgerson, filed Dec. 16, 1988.
Copending Application, Ser. No. 433,409, Bolich Jr. et al., filed Nov. 3, 1989.
Copending Application, Ser. No. 379,516, Torgerson, filed Jul. 13, 1989.
Copending Application, Ser. No. 5. 506,407, and 506,409, Wells et al., filed Apr. 6, 1990.

*Primary Examiner*—Thurman K. Page
*Attorney, Agent, or Firm*—Leonard W. Lewis; Steven J. Goldstein

[57] ABSTRACT

The present invention relates to rinse off hair conditioner compositions comprising from about 0.2% to about 20% of certain hair styling polymers, from about 0.2% to about 20% of certain non-aqueous solvents for said hair styling polymers, and from about 0.05% to about 25% of a hair conditioning agent, in an aqueous base, wherein the polymer and solvent are present in the composition as a dispersed fluid phase.

48 Claims, No Drawings

HAIR STYLING CONDITIONERS

TECHNICAL FIELD

The present invention relates to rinse off hair conditioner compositions which provide not only hair conditioning benefits, but also hair styling benefits. These are achieved by incorporating certain hair styling polymers and solvents for said polymers in a conditioner base.

BACKGROUND OF THE INVENTION

In washing, drying and styling one's hair several end results are desired. Firstly, and most obviously, one desires that the hair be thoroughly cleaned. Most desirable is a hair care process which maintains the look and feel of clean hair between hair washings. Also in the cleaning and styling process, one desires hair conditioning providing ease of combing, relief from static electricity, manageability, and soft hair feel. Generally, these benefits are provided by a separate hair conditioning product.

Finally, one desires a hair care process or product that provides hair styling benefits, especially hair style achievement and hold. The desire to have hair retain a particular shape is widely held. Such style retention is generally accomplished by either of two routes: permanent chemical alteration or temporary alteration of hair style/shape. A temporary alteration is one which can be removed by water or by shampooing. Temporary style alteration has generally been accomplished by means of the application of a third separate composition or compositions to dampened hair after shampooing and/or conditioning. The materials used to provide setting benefits have generally been resins or gums and have been applied in the form of mousses, gels, lotions, or sprays. This approach presents several significant drawbacks to the user. It requires a separate step following shampooing and conditioning to apply the styling composition. In addition, since the style hold is provided by resin materials which set-up on the hair, the hair tends to feel sticky or stiff after application and it is difficult to restyle the hair without further application of the styling composition.

It has now been discovered that two separate hair care benefits, i.e., conditioning and styling benefits, can be provided by a single hair care product. The present invention relates to rinse off hair conditioner compositions which comprise conditioners and certain hair styling agents. Rinsing with these products after shampooing provides hair conditioning and styling benefits.

It has also been discovered that the aforementioned products provide some degree of restyling benefit to the hair.

It is an object of the present invention to formulate hair care compositions which provide effective hair conditioning and styling properties.

It is also an object of the present invention to formulate hair care compositions which provide conditioning and styling benefits from a single composition.

It is a further object of the present invention to formulate hair care compositions which provide good style retention benefits without leaving hair with a stiff or sticky/tacky feel.

It is a further object of the present invention to provide an improved method for conditioning and styling hair.

These and other objects will become readily apparent from the detailed description which follows.

SUMMARY OF THE INVENTION

The present invention relates to rinse off hair conditioner compositions comprising:

a. from about 0.05% to about 25% of a hair conditioning agent;

b. from about 0.2% to about 20% of a hair styling polymer comprising:

A. from 0% to about 50% of a polymerizable hydrophilic monomer ($M_A$), or mixtures thereof; and B. from about 50% to about 100% of a polymerizable hydrophobic monomer ($M_B$), or mixtures thereof;

said polymer having a molecular weight of from about 5,000 to about 1,000,000, a Tg of greater than about $-20°$ C., and a solubility parameter, $\delta$, of from about 8.5 to about 12.0;

c. from about 0.2% to about 20% of a non-aqueous solvent which will solubilize said polymer, said solvent having a boiling point of less than or equal to about 300° C., and a solubility in water at 25° C. of greater than 0.2%; and d. the balance, an aqueous carrier;

wherein the polymer and solvent are present in the hair conditioner as a dispersed fluid phase; and wherein the ratio of polymer to solvent is from about 10:90 to about 80:20.

DETAILED DESCRIPTION OF THE INVENTION

The essential, as well as the optional, components of the present invention are described below.

Styling Agents

The conditioner compositions of the present invention contain, as an essential component, certain hair styling polymers. It is this component that provides hair styling benefits to the user.

A wide variety of hair setting polymers are generally known for use as styling agents. Many polymers said to be useful in hair styling products are multi-component polymers which combine three, four and even more different monomers into the polymer chains. Frequently, one of the monomer components is vinyl pyrrolidone. Examples of such complex polymer systems are found in U.S. Pat. No. 3,222,329 to Grosser et al., issued Dec. 7, 1965; U.S. Pat. No. 3,577,517 to Kubot et al., issued May 4, 1971; U.S. Pat. No. 4,012,501 to Farber, issued Mar. 15, 1977; U.S. Pat. No. 4,272,511 to Papantoniou and Mondet, issued Jun. 9, 1981; and U.S. Pat. No. 4,196,190, to Gehman et al., issued Apr. 1, 1980.

Other polymers said to be useful for hair styling compositions have been disclosed, such as block polymers. Examples of such block polymer systems are found in U.S. Pat. No. 3,907,984 to Calvert et al., issued Sep. 23, 1975; U.S. Pat. No. 4,030,512 to Papantoniou et al., issued Jun. 21, 1977; and U.S. Pat. No. 4,283,384 to Jacquet et al., issued Aug. 11, 1981.

It has now been found that styling polymers having water-solubilities within a certain range provide optimum hair styling benefits when delivered from a hair conditioner. The styling polymers of the present invention are of relatively low water-solubility. More specifically, these polymers have a solubility parameter, $\delta$, of between about 8.5 and about 12.0 (units equal (cal/cm$^3$)$^{\frac{1}{2}}$), preferably from about 9.5 to about 11.5, most preferably from about 11 to about 11.5.

The solubility parameter is defined in the Polymer Handbook 3rd Ed. (John Wiley and Sons, New York), J. Brandrup and E. H. Immergut, Chapter VII, pp. 519-559, as the square root of the cohesive energy density and describes the attractive strength between molecules of the material. Solubility parameters may be determined by direct measurement, correlations with other physical properties, or indirect calculation. The solubility parameters of the present polymers were determined by indirect calculations of group contributions as described in section 2.3 on p. 524-526 of the cited reference.

It has been found that styling polymers having water solubilities within this range can be dispersed with the polymer solvent, as described infra, in conditioner compositions as a dispersed fluid phase. Formulation in this way has been shown to provide maximum deposition of styling polymer out of the conditioner composition and onto hair. Styling polymers having solubility parameters at the upper end of this range would be soluble by themselves in the present conditioner compositions. It has now been found that when these polymers are combined with the polymer solvents of the present invention (as defined infra) and then dispersed in the conditioner composition, they remain in the composition as a dispersed fluid phase. Polymers having solubility parameters greater than about 12.0 will be soluble in the conditioner composition (even when they are premixed with the present polymer solvents) preventing optimum deposition of polymer on hair. Styling polymers having solubility parameters lower than about 8.5 are difficult to remove from hair and tend to build up on hair with repeated application.

The present styling polymers must comprise at least one polymerizable hydrophobic monomer. The polymer may be a homopolymer or a copolymer of hydrophobic monomers. Alternatively, the present styling polymers may be a copolymer of a hydrophilic monomer and a hydrophobic monomer, or mixtures thereof. Hence, the present hair styling polymers comprise from 0% to about 50% of a polymerizable hydrophilic monomer ($M_A$) or mixtures thereof, and from about 50% to about 100% of a polymerizable hydrophobic monomer ($M_B$), or mixtures thereof. Of course, if the styling polymer comprises both $M_A$ monomer and $M_B$ monomer, then the monomers must be copolymerizable with each other.

Preferred hydrophilic monomers of the present styling polymers include acrylic acid, methacrylic acid, N,N-dimethylacrylamide, dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (produced by the hydrolysis of vinyl acetate after polymerization), vinyl caprolactam, and mixtures thereof.

Preferred hydrophobic monomers include acrylic or methacrylic acid esters of $C_1$-$C_{18}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, and the like, the alcohols having from about 1-18 carbon atoms with the average number of carbon atoms being from about 4-12; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; methoxy ethyl methacrylate; and mixtures thereof.

Optimum performance of the present hair styling polymers in terms of style hold has been found when the weight average molecular weight of the styling polymer is between about 5,000 and about 1,000,000, preferably between about 10,000 and about 200,000 and the glass transition temperature, Tg, (i.e., the temperature at which the polymer changes from a brittle vitreous state to a plastic state) of the styling polymer is greater than about $-20°$ C., preferably between about 0° C. and about 80° C., and most preferably between about 20° C. and about 60° C.

Specific styling polymers of the present invention which provide the desired deposition/styling benefits out of a conditioner system are as follows: vinyl pyrrolidone/vinyl acetate copolymers (at ratios of up to about 30%, by weight, vinyl pyrrolidone); vinyl acetate homopolymer; t-butyl acrylate homopolymer; t-butyl styrene/ethyl hexyl methacrylate copolymer (50/50, by weight); dimethyl acrylamide/t-butyl acrylate/ethyl hexyl methacrylate copolymer (10/45/45); ethylene/vinyl acetate copolymer (12.5/87.5); allyl alcohol/styrene copolymer (19/81); vinyl chloride/vinyl acetate copolymer (83/17 and lower); vinyl pyrrolidone/vinyl acetate/butyl acrylate copolymer (10/78/12 and 10/70/20); vinyl pyrrolidone/vinyl acetate/butyl acrylate/styrene sulfonate copolymer (10/70/15/5); vinyl pyrrolidone/vinyl propionate copolymer (5/95); vinyl caprolactam/vinyl acetate copolymer (5/95); and styling resins sold under the trade names Ultrahold 8 by Ciba Geigy (ethyl acrylate/acrylic acid/N-t-butyl acrylamide copolymer), Resyn 28-1310 ® by National Starch and Luviset CA 66 ® by BASF (vinyl acetate/crotonic acid copolymer 90/10); Luviset CAP ® by BASF (vinyl acetate/vinyl propionate/crotonic acid 50/40/10); and Resyn 28-2930 ® by National Starch (vinyl acetate/vinyl neodecanoate/crotonic acid copolymer). The most preferred copolymers for use in the present invention are copolymers of vinyl pyrrolidone and vinyl acetate containing at most 30% vinyl pyrrolidone.

The polymer styling agent is present in the compositions of the present invention at a level of from about 0.2% to about 20%, preferably at a level of from about 2% to about 6%. At levels below about 0.2% styling polymer, the present hair style hold benefits cannot be achieved; at levels above about 20% styling polymer, interference with conditioning benefits may occur.

The styling polymers of the present invention formulated in the present conditioner compositions provide hair styling benefits. Such benefits include ease of style achievement and style maintenance. The present compositions also provide some degree of restyling benefits. That is, after the hair is rinsed with the present compositions and styled, the hair "remembers" the style after being subjected to a force, such as combing, brushing or simply flattening of the hair.

Polymer Solvent

A second essential component of the present conditioner compositions is a non-aqueous solvent or diluent for the styling polymer. The solvent is necessary for dilution of the polymer so that it can be dispersed in the conditioner composition. The present solvents provide optimum deposition of polymer onto hair. The solvent also aids in delivering style achievement by making polymer deposited on the hair more tacky through the hair drying and styling process. Hence, the polymer remains adhered to the hair and it enables easy manipulation of the hair into the desired style. The particular polymer chosen for use in the present conditioner compositions must be soluble in the particular solvent utilized. This enables the dispersion of the polymer/solvent mixture as a dispersed fluid phase in the conditioner composition and maintenance of that dispersed second phase. Hence, the polymer solvents of the present invention have a solubility in water at 25° C. of greater than 0.2%, preferably greater than about 0.5%, and as high as 100% soluble in water, but preferably less than 10% soluble in water. Some solvents which are completely water soluble will not remain as a dispersed fluid phase with the polymer in the conditioner composition. They will instead enter the aqueous conditioner base phase and destroy the dispersed phase of polymer and solvent in the conditioner. Many of the solvent materials of the present invention, if dispersed in the conditioner base alone, would be soluble. However, it has been found that when the solvents of the present invention are premixed with certain polymers of the present invention, prior to dispersion in the conditioner composition, they will remain in the polymer phase, i.e., unsolubilized in the conditioner base.

The polymer solvent must also be volatile. Upon deposition of the polymer/solvent mixture on the hair, the solvent is volatilized leaving only the styling polymer on the hair, thus providing the maximum styling benefits. Generally, the polymer solvents of the present invention have a boiling point of less than or equal to about 300° C.

Additionally, the polymer solvent must not interact with the polymer styling agent in such a way that would substantially reduce the ability of the polymer to provide styling benefits to hair under ordinary use situations. The solvents must, of course, be of sufficiently high purity and sufficiently low toxicity to render them suitable for administration to human hair.

The present more hydrophilic solvents are desirable for use in hair care compositions because they are safe to use, tend to have more aesthetically pleasing physical attributes, and because they tend to be less costly than other polymer solvents.

Specific polymer solvent materials that have been found to be useful in the present invention include isopropanol, butyl alcohol, amyl alcohol, phenyl ethanol, benzyl alcohol, ethyl butyrate, isopropyl butyrate, phenyl ethyl dimethyl carbinol, and mixtures thereof. Preferred solvents for use herein are benzyl alcohol, ethyl butyrate, phenyl ethanol, phenyl ethyl dimethyl carbinol, and mixtures thereof.

The amount of solvent to be used in the present conditioner compositions is an amount sufficient to solubilize the polymer and disperse it as a separate fluid phase in the conditioner composition. Generally, from about 0.2% to about 20%, preferably from about 2% to about 6%, polymer solvent is used. At levels below about 0.2% solvent, the polymer cannot be sufficiently diluted; at levels above about 20% solvent, conditioner benefits may be negatively affected. The ratio of polymer to solvent in the present compositions is from about 10:90 to about 80:20, preferably from about 40:60 to about 60:40.

European Patent Publications 0320218, published Jun. 14, 1989, and 0323715, published Jul. 12, 1989, disclose certain hair styling polymers and solvents therefor, useful in hair care compositions, including shampoos and rinse-off hair conditioners. EPO Patent Publication 0323715 teaches polymer and solvent systems having very low water solubilities (polymer is less than 0.1% soluble in water, diluent is less than 0.2% soluble in water) which are dispersed as a separate fluid phase in hair care compositions.

Conditioning Agent

The conditioner compositions of the present invention comprise, in addition to the styling polymer and solvent therefor, a conditioning agent. The conditioning agent is present in the compositions of the present invention at a level of from about 0.05% to about 25%, preferably from about 2% to about 10%. These conditioning agents may comprise conditioning agents typically used in hair conditioner compositions. Such agents generally comprise a lipid material and a cationic surfactant. These agents together provide not only hair conditioning benefits, such as anti-static, soft hair feel, and ease of combing, but also provide a gel-network thickened vehicle for the styling polymer and solvent of the present compositions. Gel-type vehicles are generally described in the following documents, all incorporated by reference herein: Barry, "The Self Bodying Action of the Mixed Emulsifier Sodium Dodecyl Sulfate/Cetyl Alcohol", 28 *J. of Colloid and Interface Science* 82-91 (1968); Barry, et al., "The Self-Bodying Action of Alkyltrimethylammonium Bromides/Cetostearyl Alcohol Mixed Emulsifiers; Influence of Quaternary Chain Length", 35 *J. of Colloid and Interface Science* 689-708 (1971); and Barry, et al., "Rheology of Systems Containing Cetomacrogol 1000—Cetostearyl Alcohol, I. Self Bodying Action", 38 *J. of Colloid and Interface Science* 616-625 (1972).

The conditioning agents may comprise one or more lipid materials which are essentially water-insoluble, and contain hydrophobic and hydrophilic moieties. Lipid materials include naturally or synthetically-derived acids, acid derivatives, alcohols, esters, ethers, ketones, and amides with carbon chains of from about 12 to about 22, preferably from about 16 to about 18, carbon atoms in length. Fatty alcohols and fatty esters are preferred; fatty alcohols are particularly preferred.

Lipid materials among those useful herein are disclosed in *Bailey's Industrial Oil and Fat Products*, (3rd edition, D. Swern, ed., 1979), incorporated by reference herein. Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, Villamarin, et al., issued May 26, 1981; British Specification 1,532,585, published Nov. 15, 1978; and Fukushima, et al., "The Effect of Cetostearyl Alcohol in Cosmetic Emulsions", 98 *Cosmetics & Toiletries* 89-112 (1983). Fatty esters included among those useful herein are disclosed in U.S. Pat. No.

3,341,465, Kaufman, et al., issued Sep. 12, 1976 (incorporated by reference herein).

Preferred esters for use herein include cetyl palmitate and glycerylmonostearate. Cetyl alcohol and stearyl alcohol are preferred alcohols. A particularly preferred lipid material is comprised of a mixture of cetyl alcohol and stearyl alcohol containing from about 55% to about 65% (by weight of mixture) of cetyl alcohol.

Cationic surfactants useful in the present conditioner compositions, contain amino or quaternary ammonium hydrophilic moieties which are positively charged when dissolved in the aqueous composition of the present invention. Cationic surfactants among those useful herein are disclosed in the following documents, all incorporated by reference herein: *McCutcheon's, Emulsifiers & Detergents,* (1989, published by the M. C. Publishing Company) Schwartz, et al., *Surface Active Agents, Their Chemistry and Technology,* New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983. If included in the compositions of the present invention, the cationic surfactant is present at from about 0.05% to about 5%.

Among the quaternary ammonium-containing cationic surfactant materials useful herein are those of the general formula:

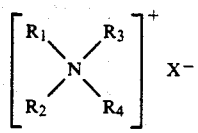

wherein $R_1$–$R_4$ are independently an aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups.

Other quaternary ammonium salts useful herein have the formula:

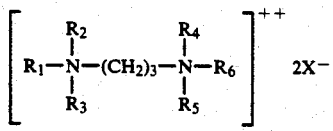

wherein $R_1$ is an aliphatic group having from about 16 to about 22 carbon atoms, $R_2$, $R_3$, $R_4$, $R_5$, and $R_6$ are selected from hydrogen and alkyl having from about 1 to about 4 carbon atoms, and X is an ion selected from halogen, acetate, phosphate, nitrate and alkyl sulfate radicals. Such quaternary ammonium salts include tallow propane diammonium dichloride.

Preferred quaternary ammonium salts include dialkyldimethylammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(hydrogenated tallow) dimethyl ammonium chloride is a particularly preferred quaternary ammonium salt.

Salts of primary, secondary and tertiary fatty amines are also preferred cationic surfactant materials. The alkyl groups of such amines preferably have from about 12 to about 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

If included in the compositions of the present invention, the lipid material is present at from about 0.1% to about 10.0% of the composition; the cationic surfactant material is present at from about 0.05% to about 5.0% of the composition.

Alternative hair conditioning agents that can be used in addition to or instead of the cationic surfactants described above are protein derivatives, such as hydrolyzed animal proteins. For example, Crotein SPA (Croda) or Lexeine X250 (Inolex) or Polypeptide LSN (Stephan) can be utilized in the present conditioner compositions. Such agents are generally present at a level of from about 0.05% to about 5.0%.

Other hair conditioning agents which can be used in addition to or instead of the above-described cationic surfactant plus lipid material are siloxane or siloxane-containing materials which are present at a level of from about 0.01% to about 10% of the conditioner composition, preferably from about 0.1% to about 5%, most preferably from about 0.2% to about 3%.

Siloxanes (see, for example, U.S. Pat. No. 3,208,911, Oppliger, issued Sep. 28, 1965) and siloxane-containing polymers have been taught for use in hair conditioning compositions. U.S. Pat. No. 4,601,902, Fridd et al., issued Jul. 22, 1986, describes hair conditioning or shampoo/conditioner compositions which include a polydiorganosiloxane having quaternary ammonium substituted groups attached to the silicon, and a polydiorgano-siloxane having silicon-bonded substituents which are amino-substituted hydrocarbon groups. U.S. Pat. No. 4,654,161, Kollmeier et al., issued Mar. 31, 1987, describes a group of organopoly-siloxanes containing betaine substituents. When used in hair care compositions, these compounds are said to provide good conditioning, compatibility with anionic components, hair substantivity, and low skin irritation. U.S. Pat. No. 4,563,347, Starch, issued Jan. 7, 1986, relates to hair conditioning compositions which include siloxane components containing substituents to provide attachment to hair. Japanese Published Application 56-129,300, Lion Corporation, published Oct. 9, 1981, relates to shampoo conditioner compositions which include an organopolysiloxaner-oxyalkylene copolymer together with an acrylic resin. U.S. Pat. No. 4,479,893, Hirota et al., issued Oct. 30, 1984, describes shampoo conditioner compositions containing a phosphate ester surfactant and a silicon derivative (e.g., polyether- or alcohol-modified siloxanes). Polyether-modified polysiloxanes are also disclosed for use in shampoos in U.S. Pat. No. 3,957,970, Korkis, issued May 18, 1976. U.S. Pat. No. 4,185,087, Morlino, issued Jan. 22, 1980, describes quaternary nitrogen derivatives of trialkylamino hydroxy organosilicon compounds which are said to have superior hair conditioning properties.

Siloxane-derived materials have also been used in hair styling compositions. Japanese Published Application 56-092,811, Lion Corporation, published Dec. 27, 1979, describes hair setting compositions which comprise an amphoteric acrylic resin, a polyoxyalkylene-denatured organopolysiloxane, and polyethylene glycol. U.S. Pat. No. 4,744,978, Homan et al., issued May 17, 1988, describes hair styling compositions (such as hair sprays) which include the combination of a carboxyfunctional polydimethyl-siloxane and a cationic organic polymer containing amine or ammonium groups. Hair styling compositions which include poly-diorganosiloxanes and a cationic organic polymer are taught in U.S. Pat. No. 4,733,677, Gee et al., issued Mar. 29, 1988, and U.S. Pat. No. 4,724,851, Cornwall et al., issued Feb. 16, 1988. Finally, European Patent Application 117,360, Cantrell et al., published Sep. 5, 1984, discloses compositions, containing a siloxane polymer having at least one nitrogen-hydrogen bond, a surfactant, and a solubilized titanate, zirconate or germanate, which act as both a conditioner and a hair styling aid.

Nonvolatile silicone fluids are useful as the conditioning agent component in the compositions of the present invention. Examples of such materials include polydimethylsiloxane gums and fluids, aminosilicones and phenylsilicones. More specifically, materials such as polyalKyl or polyaryl siloxanes with the following structure:

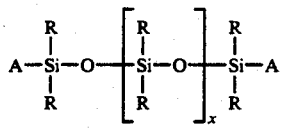

wherein R is alkyl or aryl, and x is an integer from about 7 to about 8,000 may be used. A represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

Suitable methods for preparing these silicone materials are disclosed in U.S. Pat. Nos. 2,826,551 and 3,964,500 and references cited therein. Silicones useful in the present invention are also commercially available. Suitable examples include Viscasil, a trademark of the General Electric Company and silicones offered by Dow Corning Corporation and by SWS Silicones, a division of Stauffer Chemical Company.

Other useful silicone conditioning materials include materials of the formula:

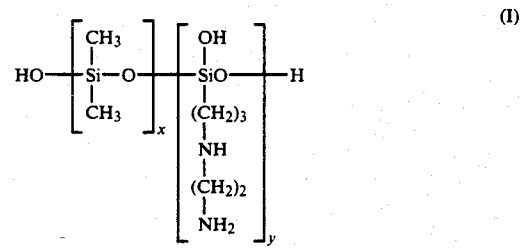

in which x and y are integers which depend on the molecular weight, the average molecular weight being approximately between 5,000 and 10,000. This polymer is also known as "amodimethicone".

Other silicone cationic polymer conditioning agents which can be used in the present compositions correspond to the formula:

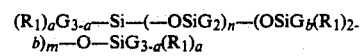

in which G is chosen from the group consisting of hydrogen, phenyl, OH, $C_1$–$C_8$ alkyl and preferably methyl; a denotes 0 or an integer from 1 to 3, and preferably equals 0;

b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10;

$R_1$ is a monovalent radical of formula $C_qH_{2q}L$ in which q is an integer from 2 to 8 and L is chosen from the groups

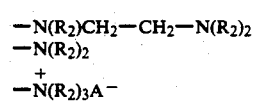

-continued

in which $R_2$ is chosen from the group consisting of hydrogen, phenyl, benzyl, a saturated hydrocarbon radical, preferably an alkyl radical containing from 1 to 20 carbon atoms, and $A^-$ denotes a halide ion.

These compounds are described in greater detail in European Patent Application EP 95,238. An especially preferred polymer corresponding to this formula is the polymer known as "trimethylsilylamodimethicone" of formula:

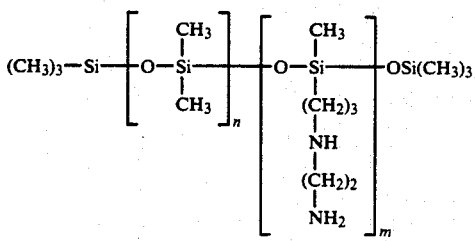

Other silicone cationic polymer conditioning agents which can be used in the present compositions correspond to the formula:

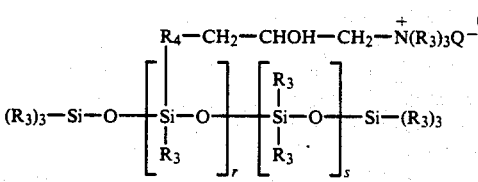

in which $R_3$ denotes a monovalent hydrocarbon radical having from 1 to 18 carbon atoms, and more especially an alkyl or alkenyl radical such as methyl; $R_4$ denotes a hydrocarbon radical such as, preferably a $C_1$-$C_{18}$ alkylene radical or a $C_1$-$C_{18}$, and preferably $C_1$-$C_8$, alkyleneoxy radical;

$Q^-$ is a halide ion, preferably chloride;

r denotes an average statistical value from 2 to 20, preferably from 2 to 8;

s denotes an average statistical value from 20 to 200, and preferably from 20 to 50.

These compounds are described in greater detail in U.S. Pat. No. 4,185,017.

A polymer of this class which is especially preferred is that sold by UNION CARBIDE under the name "UCAR SILICONE ALE 56".

Conditioning agent materials also useful in the compositions of the present invention are silicone polymer materials which provide both style retention and conditioning benefits to the hair. These materials comprise rigid silicone polymers.

Some examples of such materials include, but are not limited to, filler reinforced polydimethyl siloxane gums including those having end groups such as hydroxyl; cross linked siloxanes, such as organic substituted silicone elastomers; organic substituted siloxane gums, including those having end groups such as hydroxyl; and resin reinforced siloxanes.

The rigid silicone polymers useful in the present invention have complex viscosities of at least $2 \times 10^5$ poise (P), preferably about $1 \times 10^7$ poise, where complex viscosity is measured by subjecting a sample to oscillatory shear at a fixed frequency of 0.1 rad/sec at 25° C. using a Rheometric Fluids Spectrometer ® measuring films having a thickness of about 1 millimeter. The resulting viscous and elastic force responses are combined to determine the complex modulus which is divided by the imposed frequency to compute the complex viscosity.

A preferred siloxane gum useful in the present invention is a diphenyl-dimethyl polysiloxane gum having a molecular weight of at least about 500,000, and must be diphenyl substituted to the extent of 3% or more, preferably at least about 5%.

The siloxane gums may also be filler reinforced to provide additional rigidity. Silica is the preferred filler. Generally such reinforced gums comprise up to about 15-20% silica.

Silicone resins also useful in formulating the rigid silicones in the present compositions are silicone polymers with a high degree of crosslinking introduced through the use of trifunctional and tetrafunctional silanes. Typical silanes used in the manufacture of resins are monomethyl, dimethyl, monophenyl, diphenyl, methylphenyl, monovinyl, and methylvinyl chlorosilanes, together with tetrachlorosilane. A preferred resin is one offered by General Electric as GE SR545. This resin is provided as a solution in toluene which is stripped prior to the resin's use. This resin is used in combination with the siloxane gum to provide extra rigidity.

Other rigid silicone polymers of use herein are those siloxanes which have been sparingly crosslinked but are still soluble in solvents such as cyclomethicone. Precursors for the rigid material can be any high molecular weight polydimethyl siloxanes, polydimethyl siloxanes containing vinyl groups and other siloxanes. Methods of crosslinking include heat curing with organic peroxides such as dibenzoyl peroxide and di-t-butyl peroxide, heat vulcanization with sulfur, and high-energy radiation.

Obviously, the silicone conditioning agent should be selected such that it does not interfere with the hair style holding performance of the styling polymers of the present invention. Preferably the silicone conditioning agent comprises a polydimethylsiloxane gum, having a viscosity greater than about 1,000,000 centipoise and a dimethicone fluid having a viscosity of from about 2 centipoise to about 100,000 centipoise, wherein the ratio of gum to fluid is from about 30:70 to about 70:30, preferably from about 40:60 to about 60:40.

Alternatively, the hair styling agent and hair conditioning agent of the present compositions can be provided by a single material. Examples of such materials are copolymers having siloxane macromers grafted thereto, which meet the functional limitations as defined supra. That is, the non-silicone backbone of such polymers should have a molecular weight of from about 5,000 to about 1,000,000, a Tg of greater than about −20° C., and a solubility parameter of from about 8.5 to about 12.0.

Preferred polymers comprise a polymeric backbone and, grafted to the backbone, a polydimethylsiloxane macromer having a weight average molecular weight of from about 1,000 to about 50,000, preferably from about 5,000 to about 40,000, most preferably about 10,000. The polymer is such that when it is formulated into the finished hair care composition used to treat the hair, and then the hair dried, the polymer phase separates into a discontinuous phase which includes the polydimethylsiloxane macromer and a continuous phase which includes the backbone. It is believed that this phase separation property provides a specific orientation of the polymer on hair which results in the desired hair conditioning and setting benefits.

In its broadest aspect, the copolymers comprise C monomers together with monomers selected from the group consisting of A monomers, B monomers, and mixtures thereof. These copolymers contain at least A or B monomers together with C monomers, and preferred copolymers contain A, B and C monomers.

Examples of useful copolymers and how they are made are described in detail in U.S. Pat. No. 4,693,935, Mazurek, issued Sep. 15, 1987, and U.S. Pat. No. 4,728,571, Clemens et al., issued Mar. 1, 1988, both of which are incorporated herein by reference. These copolymers are comprised of monomers A, C and, optionally, B, which are defined as follows. A, is at least one free radically polymerizable vinyl monomer or monomers. B, when used, comprises at least one monomer copolymerizable with A. When used, B may be up to about 30%, preferably up to about 10%, more preferably 5%, of the total monomers in the copolymer. Monomer C comprises from about 0.01% to about 50.0% of the total monomers in the copolymer.

Representative examples of A monomers are the same as the hydrophobic monomers described supra for the styling polymers of the present invention which do not comprise siloxane macromers.

Representative examples of B monomers are the same as the hydrophilic monomers described supra for the styling polymers of the present invention which do not comprise siloxane macromers.

The C monomer has the general formula:

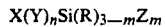

wherein X is a vinyl group copolymerizable with the A and B monomers; Y is a divalent linking group; R is a hydrogen, lower alkyl, aryl or alkoxy; Z is a monovalent siloxane polymeric moiety having a number average molecular weight of at least about 500, is essentially unreactive under copolymerization conditions and is pendant from the vinyl polymeric backbone, described above; n is 0 or 1; and m is an integer from 1 to 3° C. has a weight average molecular weight of from about 1,000 to about 50,000, preferably from about 5,000 to about 40,000, most preferably about 10,000. Preferably, the C monomer has a formula selected from the following group:

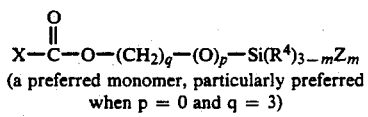

(a preferred monomer, particularly preferred when p = 0 and q = 3)

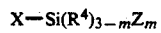

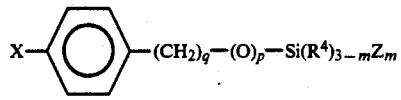

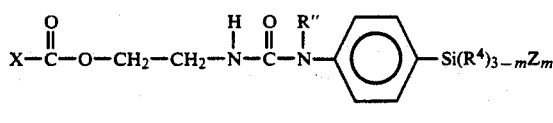

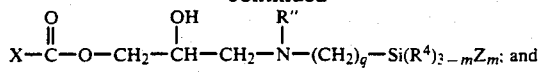

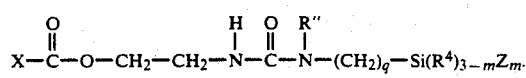

In those structures, m is 1, 2 or 3 (preferably m=1); p is 0 or 1; R" is alkyl or hydrogen; q is an integer from 2 to 6; s is an integer from 0 to 2; X is

$R^1$ is hydrogen or —COOH (preferably $R^1$ is hydrogen); $R^2$ is hydrogen, methyl or —CH$_2$COOH (preferably $R^2$ is methyl); Z is

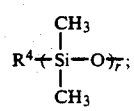

$R^4$ is alkyl, alkoxy, alkylamino, aryl, or hydroxyl (preferably $R^4$ is alkyl); and r is an integer from about 5 to about 700 (preferably r is about 250).

The preferred of these siloxane containing copolymers generally comprise from 50% to about 98% (preferably from about 85% to about 98%, more preferably from about 90% to about 97%) of monomer A, from 0% to about 30% (preferably from about 2% to about 8%) of monomer B, and from about 0.1% to about 50% (preferably from about 0.5% to about 20%, most preferably from about 2% to about 10%) of monomer C. The combination of the A and B monomers preferably comprises from about 50.0% to about 99.9% (more preferably about 80% to about 99%, most preferably from about 90% to about 98%) of the polymer.

Specific polymers which may be used in the present invention include the following (the weight percents below refer to the amount of reactants added in the polymerization reaction, not necessarily the amount in the finished polymer):

polyvinyl pyrrolidone/vinyl acetate/polydimethylsiloxane (PDMS) macromer - 10,000 molecular weight (5/90/5 w/w/w) (I)

acrylic acid/n-butylmethacrylate/polydimethylsiloxane (PDMS) macromer-20,000 molecular weight (10/70/20 w/w/w) (II)

N,N-dimethylacrylamide/isobutyl methacrylate/PDMS macromer-20,000 molecular weight (20/60/20 w/w/w) (III)

t-butylacrylate/PDMS macromer-10,000 molecular weight (80/20 w/w) (IV)

t-butylacrylate/N,N-dimethylacrylamide/PDMS macromer-10,000 molecular weight (70/10/20 w/w/w) (V)

t-butylacrylate/acrylic acid/PDMS macromer-10,000 molecular weight (75/5/20 w/w/w) (VI)

polyvinyl pyrrolidone/vinyl acetate/polydimethylsiloxane-20,000 molecular weight (4/95/1 w/w/w) (VII)

polyvinyl pyrrolidone/vinyl acetate/polydimethyl siloxane-20,000 molecular weight (2.5/95/2.5 w/w/w) (VIII)

As with the non-siloxane containing styling polymers described supra, the present copolymers must be diluted with a polymer solvent of the present invention prior to combination with the remaining conditioner composition ingredients. This will enable the formation of a dispersed phase of polymer and solvent in the conditioner composition.

When these siloxane containing copolymers are used in the conditioner compositions of the present invention to act as both a hair styling polymer and hair conditioning agent, they are generally present at a level of from about 0.2% to about 20%, preferably from about 2% to about 6%.

Most preferably these materials which act as both the hair styling polymer and hair conditioning agent in the present compositions comprise a polyvinyl pyrrolidone/polydimethyl siloxane/vinyl acetate copolymer wherein the non-silicone backbone of the copolymer has a molecular weight of from about 10,000 to about 200,000, a $T_g$ of from about 20° C. to about 60° C., and a solubility parameter, $\delta$, of from about 11.0 to about 11.5.

The present silicone conditioning agents can be used in conditioner vehicle systems thickened with materials other than the lipid material plus cationic surfactant gel-network vehicle systems described supra.

Nonionic water-soluble cellulose ethers have been employed as thickeners in hair care compositions. Widely used, commercially-available nonionic cellulose ethers include methyl cellulose, hydroxy propyl methyl cellulose, hydroxyethyl cellulose, hydroxypropyl cellulose and ethyl hydroxyethyl cellulose.

Better thickening efficiency is realized with higher molecular weight cellulose ethers. However, production of such materials is difficult and expensive. Though crosslinking of these polymers is an alternative means to achieve high viscosity solutions, good crosslinking techniques are not known. Of course, high concentrations of polymers will also provide high viscosity but such an approach is inefficient and impractical, particularly due to the high expense involved. Furthermore, use of highly crosslinked polymers or high levels of polymeric thickeners may result in a vehicle system that is too elastic for the present uses.

Alternative water-soluble polymeric thickeners sometimes used to thicken conditioner compositions are natural polysaccharides such as guar gum, xanthan gum and locust bean gum.

A number of references teach the use of nonionic cellulose ethers and water-soluble gums for thickening hair care compositions. See for example, U.S. Pat. No. 4,557,928, Glover, issued Dec. 10, 1985, teaching a hair conditioner comprising a suspension system which consists of one of glucan gum, guar gum, and hydroxyethylcellulose; and U.S. Pat. No. 4,581,230, Grollier et al., issued Apr. 8, 1986, which teaches cosmetic compositions for treating hair which comprise as thickening agents hydroxyethylcellulose, or water-soluble vegetable thickening agents, such as guar gum. Japanese Patent Publication 61-053211, published Mar. 7, 1986, discloses a hair colorant containing an aromatic alcohol, xanthan gum, and hydroxyethylcellulose.

Certain cellulose ethers have been disclosed in U.S. Pat. No. 4,228,277, Landoll, issued Oct. 14, 1980, which are relatively low molecular weight but which are capable of producing highly viscous aqueous solutions in practical concentrations. These materials are nonionic cellulose ethers having a sufficient degree of nonionic substitution selected from the group consisting of methyl, hydroxyethyl, and hydroxypropyl to cause them to be water-soluble and which are further substituted with a hydrocarbon radical having from about 10 to 24 carbon atoms in an amount between about 0.2 weight percent and the amount which renders said cellulose ether less than 1%, by weight, soluble in water. The cellulose ether to be modified is preferably one of low to medium molecular weight; i.e., less than about 800,000 and preferably between about 20,000 and 700,000 (about 75 to 2500 D.P.).

The Landoll patent teaches that any nonionic water-soluble cellulose ether can be employed as the cellulose ether substrate. Thus, e.g., hydroxyethyl cellulose, hydroxypropyl cellulose, methyl cellulose, hydroxypropyl methyl cellulose, ethyl hydroxyethyl cellulose, and methyl hydroxyethyl cellulose can all be modified. The amount of nonionic substituent such as methyl, hydroxyethyl or hydroxypropyl is taught not to be critical so long as there is an amount sufficient to assure that the ether is water-soluble.

The preferred cellulose ether substrate is hydroxyethyl cellulose (HEC) of about 50,000 to 700,000 molecular weight. Hydroxyethyl cellulose of this molecular weight level is the most hydrophilic of the materials contemplated. It can thus be modified to a greater extent than can other water-soluble cellulose ether substrates before insolubility is achieved. Accordingly, control of the modification process and control of the properties of the modified product can be more precise with this substrate. Hydrophilicity of the most commonly used nonionic cellulose ethers varies in the general direction: hydroxyethyl→hydroxypropyl→hydroxypropyl methyl→methyl.

The long chain alkyl modifier can be attached to the cellulose ether substrate via an ether, ester or urethane linkage. The ether linkage is preferred.

Although the materials taught in Landoll are referred to as being "long chain alkyl group modified", it will be recognized that except in the case where modification is effected with an alkyl halide, the modifier is not a simple long chain alkyl group. The group is actually an alphahydroxyalkyl radical in the case of an epoxide, a urethane radical in the case of an isocyanate, or an acyl radical in the case of an acid or acyl chloride. Nonetheless, the terminology "long chain alkyl group is used since the size and effect of the hydrocarbon portion of the modifying molecule completely obscure any noticeable effect from the connecting group. Properties are not significantly different from those of the product modified with the simple long chain alkyl group.

One commercially available material which meets these requirements is NATROSOL PLUS Grade 430, hydrophobically modified hydroxyethylcellulose available from Aqualon Company, Wilmington, Delaware. This material has a $C_{16}$ a alkyl substitution of about 0.5% to about 0.9% by weight. The hydroxyethyl molar substitution for this material is from about 2.8 to about 3.2. The average molecular weight for the water-soluble cellulose prior to modification is approximately 300,000.

The most preferred material of this type is sold under the trade name NATROSOL PLUS CS Grade D-67, by Aqualon Company, Wilmington, Del. This material has a $C_{16}$ a alkyl substitution of from about 0.50% to about 0.95%, by weight. The hydroxyethyl molar substitution for this material is from about 2.3 to about 3.3. The average molecular weight for the water-soluble cellulose prior to modification is approximately 700,000.

These modified cellulose ethers have been disclosed for use in a variety of composition types. Landoll ('277) teaches the use of these materials in shampoo formulations. Hercules trade literature teaches the use of these materials in shampoos. U.S. Pat. No. 4,683,004, Goddard, issued Jul. 28, 1987, discloses the use of these materials in mousse compositions for the hair.

These materials can be used with certain secondary thickening materials to provide a rheology very much like the gel-network structure provided by lipid material plus cationic surfactant based conditioner compositions described supra.

The first of these secondary thickening materials is a water-soluble polymeric material, having a molecular weight greater than about 20,000. By "water-soluble polymer" is meant that the material will form substantially a clear solution in water at a 1% concentration at 75° C. and the material will increase the viscosity of the water. Examples of water-soluble polymers which are desirably used as the additional thickening component in the present vehicle systems, include hydroxyethylcellulose, hydroxypropyl cellulose, hydroxypropyl methylcellulose, polyethylene glycol, polyacrylamide, polyacrylic acid, polyvinyl alcohol, polyvinyl pyrrolidone K-120, dextrans, for example Dextran purified crude Grade 2P, available from D&O Chemicals, carboxymethylcellulose, plant exudates such as acacia, ghatti, and tragacanth, seaweed extracts such as sodium alginate, propylene glycol alginate, sodium carrageenan, and Ucare JR-polymer (a cationic modified hydroxyethyl cellulose available from Union Carbide). Preferred as the additional thickener for the present vehicle systems are natural polysaccharide materials. Examples of such materials are guar gum, locust bean gum, and xanthan gum. Also preferred as the additional thickener in the present compositions is hydroxyethylcellulose having a molecular weight of about 700,000.

When such systems are used to thicken the present compositions, from about 0.3% to about 5.0%, preferably from about 0.4% to about 3.0% of the hydrophobically modified hydroxyethyl cellulose is utilized with from about 0.3% to about 5.0%, preferably from about 0.4% to about 3.0% of the water-soluble polymeric material.

An alternative secondary thickening material for the hydrophobically modified hydroxyethyl cellulose is a water-soluble surfactant having a molecular weight of less than about 20,000. By "water-soluble surfactant" is meant surfactant materials which form clear isotropic solutions when dissolved in water at 0.2 weight percent at ambient conditions.

Essentially any water-soluble surfactant material which meets these requirements will work in the present invention. However, the following materials have been found to be particularly preferred: cetyl betaine, ammonium lauryl sulfate, ammonium laureth sulfate, cetyl trimethyl ammonium chloride, and mixtures thereof.

When such systems are used to thicken the present compositions, from about 0.1% to about 10.0%, preferably from about 0.2% to about 5.0% of the hydrophobically-modified hydroxyethyl cellulose is utilized with from about 0.02% to about 0.30%, preferably from about 0.05% to about 0.30%, most preferably from about 0.05% to about 0.20%, of the water-soluble surfactant. The water-soluble surfactant level is kept low because higher levels of water-soluble surfactants interfere with the hydrophobically-modified hydroxyethyl cellulose thickener and produce compositions with much less desirable rheologies.

A final alternative secondary thickening material for the hydrophobically-modified hydroxyethyl cellulose is a water-insoluble surfactant having a molecular weight of less than about 20,000. By "water-insoluble surfactant" is meant surfactant materials which do not form clear isotropic solutions when dissolved in water at greater than 0.2 weight percent at ambient conditions.

Essentially any water-insoluble surfactant material which meets these requirements will work in the present invention. However, the following materials have been found to be particularly preferred: stearamide DEA, cocoamide MEA, dimethyl stearamine oxide, glyceryl monooleate, sucrose stearate, PEG-2 stearamine, Ceteth-2, a polyethylene glycol ether of cetyl alcohol of the formula $CH_3-(CH_2)_{14}-CH_2-(OCH_2CH_2)_n-OH$, where n has an average value of 2 (commercially available under the trade name Brij 56 from ICI Americas), glycerol stearate citrate, dihydrogenated tallow dimethyl ammonium chloride, Poloxamer 181, a polyoxyethylene, polyoxypropylene block polymer of the formula

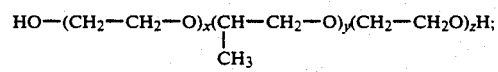

wherein on average $x=3$, $y=30$ and $z=3$ (commercially available from BASF Wyandotte under the trade name Pluronic L-61), hydrogenated tallow dimethyl betaine, and hydrogenated tallow amide DEA.

When such systems are used to thicken the present compositions, from about 0.1% to about 10.0%, preferably from about 0.2% to about 5.0% of the hydrophobically-modified hydroxyethyl cellulose is utilized with from about 0.02% to about 10.0%, preferably from about 0.05% to about 3.0%, most preferably from about 0.05% to about 2.0%, of the water-insoluble surfactant.

The conditioner compositions of the present invention which are thickened with the hydrophobically-modified hydroxyethyl cellulose plus secondary thickening materials, as described above preferably also contain a material which provides additional rheological benefits to the cosmetic compositions formulated therewith. These materials are chelating agents. In general, such materials include monodentate and multidentate agents. Specific examples of useful chelating agents include ethylene-diaminetetraacetic acid (EDTA), and salts thereof, nitrilotriacetic acid (NTA) and salts thereof, hydroxyethyl ethylene diamine triacetic acid (HEEDTA) and salts thereof, diethylene triamine pentaacetic acid (DTPA) and salts thereof, diethanolglycine (DEG) and salts thereof, ethanol diglycine (EDG) and salts thereof, citric acid and salts thereof, phosphoric acid and salts. The most preferred of these is EDTA. The chelating agents tend to make the vehicle systems useful in the present invention smoother and less gelatinous in consistency.

If a chelating agent is present as a rheological aid in the compositions of the present invention it is present at a level of from about 0.05% to about 1.0%, preferably from about 0.05% to about 0.3%, of the composition.

An additional component which may be used in the conditioner compositions of the present invention which are thickener with the hydrophobically modified hydroxyethyl cellulose plus secondary thickening materials, as described above, is a material which acts as a distributing aid for the composition. Such a material helps to distribute the composition onto the hair avoiding localized deposition of the conditioning and styling components onto the hair. Without such a component in a composition, some components in the composition would not be deposited and spread out as evenly, and hence, would not be quite as effective.

Distributing aid materials useful in the present invention are actually a subclass of the class of materials which can be used as the water-soluble polymer secondary thickener in the present invention. This subclass is defined as follows: water-soluble polymer materials having high molecular weight, i.e., greater than 1,000,000; and/or strong ionic character. By strong ionic character is meant that the material conducts electricity at greater than 30 millivolts. This can be measured by evaluating conductance of a 1% solution of polymer in DRO (double reverse osmosis) water preserved with 0.03% Kathon CG (a preservative available from Rohm & Haas) using a calibrated Corning 130 pH meter. The probes used were as follows: the reference electrode is an Orion Model 9001 single junction. The pH electrode is an Orion Model 9161, silver-silver chloride. The probes are set 3/8 of an inch apart. The pH meter is set to millivolt readings. The absolute measurement is recorded after 4 minutes immersion.

Examples of water soluble polymer materials which meet these requirements and hence, can act as distributing aids in the present compositions include xanthan gum; Dextran purified crude Grade 2P available from D&O chemicals; carboxymethyl celluloses; for example, CMC's 4HIF, 4M6F, 7HF, 7M8SF, 7LF, 9H4F, 9M8, 12M8P, 16M31, (all available from Aqualon); plant exudates such as acacia, ghatti and tragacanth; seaweed extracts such as sodium alginate, propylene glycol alginate, and sodium carrageenan; high molecular weight hydroxyethyl celluloses such as Natrosol 250H and Natrosol 250HHR (available from Aqualon); and pectin.

Because the class of materials which may act as distributing aids in the present compositions is a subset of the optional water-soluble polymer secondary thickener, the materials in this subclass may be used to provide both benefits to the composition. For example, xanthan gum is a water-soluble natural polysaccharide material which additionally has a high molecular weight. Hence, this material could be used by itself to provide both additional thickening benefits and distributing benefits. However, it may be necessary to use such materials at slightly higher levels to provide both benefits.

It is also possible to use two separate materials as the optional water-soluble polymer secondary thickener and the distributing aid of the present invention. This would be done when the water-soluble polymer secondary thickener was not a high molecular weight material or of strong ionic character. Locust bean gum is such a material. A distributing aid such as xanthan gum could be used with locust bean gum to provide the additional distributing benefits.

If a distributing aid is present in the conditioning compositions of the present invention, it should be present at a level of from about 0.02% to about 2.5%, preferably from about 0.05% to about 1.0%, of the cosmetic composition. If the distributing aid is bifunctional, i.e., acting as both the optional secondary thickener and the distributing aid it should be present at a level of from about 0.2% to about 5.0% of the composition.

The hair conditioner compositions herein can contain a variety of other optional components suitable for rendering such compositions more cosmetically or aesthetically acceptable or to provide them with additional usage benefits. Such conventional optional ingredients are well-known to those skilled in the art, e.g., pearlescent aids, such as TiOz coated mica, ethylene glycol distearate, and PEG 3 distearate; opacifiers; preservatives, such as benzyl alcohol, Glydant, Kathon, methyl paraben, propyl paraben and imidazolidinyl urea; fatty alcohols, such as cetearyl alcohol; sodium chloride; sodium sulfate; polyvinyl alcohol; ethyl alcohol; pH adjusting agents, such as citric acid, sodium citrate, succinic acid, phosphoric acid, monosodium phosphate, disodium phosphate, sodium hydroxide, and sodium carbonate; coloring agents, such as any of the FD&C or D&C dyes; perfumes; sequestering agents, such as disodium ethylenediamine tetra-acetate; and polymer plasticizing agents, such as glycerin and propylene glycol. The present compositions can also optionally comprise thickeners and viscosity modifiers, such as a diethanolamide of a long chain fatty acid (e.g., PEG 3 lauric diethanolamide), lauramide DEA, cocomonoethanol amide, dimethicone copolyols, guar gum, xanthan gum, methyl cellulose, hydroxyethyl cellulose, starches and starch derivatives. Such optional ingredients generally are used individually at levels of from about 0.01% to about 10.0%, preferably from about 0.05% to about 5.0%, of the conditioner composition.

As with all compositions, the present invention should not contain optional components which unduly interfere with the conditioning and hair style holding performance of the present conditioner compositions.

Aqueous Carrier

The balance of the present conditioner compositions comprises water or water combined with some other carrier substance which does not interfere with the conditioning and style hold benefits of the present compositions.

Method of Making

The hair conditioner compositions of the present invention can be made using conventional formulation and mixing techniques. The polymer must first be dissolved in the polymer solvent. The remaining ingredients are combined in a separate vessel and the polymer/solvent mixture is added. Methods of making various types of hair conditioner compositions are described in the following examples.

Method of Use

The hair conditioner compositions of the present invention are used in conventional ways to provide the hair conditioning and styling hold benefits of the present invention. Such method generally involves application of an effective amount of the conditioner product to wet shampooed hair, which is massaged through and then rinsed from the hair. By "effective amount" is meant an amount sufficient to provide the hair conditioning and style hold benefits desired considering the length and texture of the hair. After the hair is treated with the compositions of the present invention, the hair is dried and styled in the usual ways of the user.

The following examples illustrate the present invention. It will be appreciated that other modifications of the present invention within the skill of those in the cosmetic composition formulation art can be undertaken without departing from the spirit and scope of this invention.

All parts, percentages, and ratios herein are by weight unless otherwise specified.

EXAMPLE I

The following is a rinse-off hair conditioner composition representative of the present invention.

| Component | Weight % |
|---|---|
| Natrosol Plus CS Grade D-67[1] | 0.60 |
| Locust bean gum | 0.50 |
| EDTA, disodium salt | 0.15 |
| DTDMAC | 0.65 |
| Glydant | 0.40 |
| Styling Polymer/Solvent Premix | |
| Polyvinylpyrrolidone/Vinyl Acetate (5/95) | 3.00 |
| Benzyl Alcohol | 3.00 |
| Silicone Conditioning Agent Premix | |
| Dimethicone Gum[2] | 0.50 |
| Decamethyl cyclopenta siloxane | 2.83 |
| Water | q.s. to 100% |

[1]Hydrophobically-modified hydroxyethyl cellulose commercially available from Aqualon Co.
[2]SE-76 dimethicone gum available from GE Silicones This product is prepared by first dissolving the polyvinyl-pyrrolidone/vinyl acetate (5/95) copolymer in the benzyl alcohol. The dimethicone gum and decamethyl cyclopenta siloxane are also separately premixed. The remaining components are combined in a separate vessel with heating and stirring. The polymer/solvent mixture and silicone conditioning agent premix are then added to the remaining components either hot or after they have been cooled.

This conditioner product provides hair conditioning and hair style holding benefits.

EXAMPLE II

The following is a rinse-off hair conditioner composition representative of the present invention.

| Component | Weight % |
|---|---|
| Styling Polymer/Solvent Premix | |
| Poly t-Butyl Acrylate (MW = 100,000) | 1.50 |
| Ethyl n-Butyrate | 2.50 |
| Stearalkonium Chloride | 3.80 |
| Cetyl Alcohol | 1.35 |
| Stearyl Alcohol | 1.35 |
| Ceteth-2 | 0.80 |
| Glyceryl Stearate | 0.50 |
| Quaternized hydrolyzed protein | 0.50 |
| Citric Acid | 0.11 |
| Sodium Chloride | 0.10 |
| Kathon CG | 0.03 |
| Water | q.s. to 100% |

This product is prepared by first dissolving the poly-t-butyl acrylate in the ethyl n-butyrate. The remaining components are combined in a separate vessel with heating and stirring. The polymer/solvent mixture is then added to the remaining components either hot or after they have been cooled.

This conditioner product provides hair conditioning and hair style holding benefits.

EXAMPLE III

The following is a rinse-off hair conditioner composition representative of the present invention.

| Component | Weight % |
|---|---|
| Styling Polymer/Solvent Premix | |
| Polyvinylpyrrolidone/vinyl acetate (30/70) | 4.0 |
| Isopropanol | 5.0 |
| Silicone Conditioning Agent 5.0 | |
| Dimethicone Gum[1] | 0.30 |
| Decamethyl cyclopenta siloxane | 1.70 |
| DTDMAC | 0.85 |
| Hydroxyethyl cellulose | 0.50 |
| Cetyl Alcohol | 0.90 |
| Stearyl Alcohol | 0.80 |
| Ceteareth-20 | 0.50 |
| Lexamine S13 | 0.15 |
| Glyceral Monostearate | 0.50 |
| Citric Acid | 0.11 |
| Kathon | 0.03 |
| Water | q.s. to 100% |

[1]SE-76 available from GE Silicones

This product is prepared using the method described in Example I.

This conditioner product provides hair conditioning and hair style holding benefits.

EXAMPLE IV

The following is a rinse-off hair conditioner composition representative of the present invention.

| Component | Weight % |
|---|---|
| N,N-dimethylacrylamide/isobutyl methacrylate/ethyl hexyl methacrylate/10K silicone macromer - copolymer (30/30/20/20) | 2.00 |
| Diethyl Phthalate | 6.00 |
| DTDMAC | 0.90 |
| Cetyl Alcohol | 1.10 |
| Stearyl Alcohol | 0.70 |
| Ceteareth-20 | 0.60 |
| Glyceryl Monostearate | 0.50 |
| Citric Acid | 0.11 |
| Kathon | 0.03 |
| Water | q.s. to 100% |

This product is prepared by first dissolving the styling copolymer in the diethyl phthalate. The remaining components are combined in a separate vessel with heating and stirring to melt the solids. The polymer/solvent mixture is then added to the remaining components either hot or after they have been cooled.

This conditioner product provides hair conditioning as well as hair style hold benefits.

What is claimed is:

1. A rinse-off hair conditioner composition comprising:
   a. from about 0.05% to about 25% of a hair conditioning agent;
   b. from about 0.2% to about 20% of a hair styling polymer comprising:
      A. from 0% to about 50% of a polymerizable hydrophilic monomer ($M_A$), or mixtures thereof; and
      B. from about 50% to about 100% of a polymerizable hydrophobic monomer ($M_B$), or mixtures thereof;

said polymer having a weight average molecular weight of from about 5,000 to about 1,000,000, a Tg of greater than about $-20°$ C., and a solubility parameter, $\delta$, of from about 8.5 to about 12.0; and c. from about 0.2% to about 20% of a non-aqueous solvent which will solubilize said polymer, said solvent having a boiling point of less than or equal to about 300° C., and a solubility in water at 25° C. of greater than 0.2%; and d. the balance, an aqueous carrier;

wherein the polymer and solvent are present in the hair conditioner composition as a dispersed fluid phase; and wherein the ratio of polymer to solvent is from about 10:90 to about 80:20.

2. The hair conditioner composition of claim 1 wherein $\delta$ is from about 9.5 to about 11.5.

3. The hair conditioner composition of claim 2 wherein $\delta$ is from about 11 to about 11.5.

4. The hair conditioner composition of claim 3 wherein the hydrophobic monomer is selected from the group consisting of acrylic acid esters of $C_1$-$C_{18}$ alcohols; methacrylic acid esters of $C_1$-$C_{18}$ alcohols; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; methoxyethyl methacrylate; and mixtures thereof.

5. The hair conditioner composition of claim 3 wherein the hair styling polymer comprises both the polymerizable hydrophilic monomer and the polymerizable hydrophobic monomer.

6. The hair conditioner composition of claim 5 wherein the hydrophilic monomer is selected from the group consisting of acrylic acid, methacrylic acid, N,N-dimethylacrylamide, dimethylaminoethyl methacrylate, methacrylamide, N-t-butyl acrylamide, maleic acid, maleic anhydride, half esters of maleic anhydride, crotonic acid, itaconic acid, acrylamide, acrylate alcohols, hydroxyethyl methacrylate, vinyl pyrrolidone, vinyl ethers, maleimides, vinyl pyridine, vinyl imidazole, styrene sulfonate, allyl alcohol, vinyl alcohol, vinyl caprolactam, and mixtures thereof.

7. The hair conditioner composition of claim 6 wherein the hydrophobic monomer is selected from the group consisting of acrylic acid esters of $C_1$-$C_{18}$ alcohols; methacrylic acid esters of $C_1$-$C_{18}$ alcohols; styrene; polystyrene macromer; vinyl acetate; vinyl chloride; vinylidene chloride; vinyl propionate; alphamethylstyrene; t-butylstyrene; butadiene; cyclohexadiene; ethylene; propylene; vinyl toluene; methoxy ethyl methacrylate; and mixtures thereof.

8. The hair conditioner composition of claim 1 wherein the hair styling polymer is selected from the group consisting of vinyl pyrrolidone/vinyl acetate copolymer; t-butyl acrylate homopolymer; t-butyl styrene/ethyl hexyl methacrylate copolymer (50/50); dimethyl acrylamide/t-butyl acrylate/ethyl hexyl methacrylate copolymer (10/45/45); ethylene/vinyl acetate copolymer (12.5/ 87.5); styrene/allyl alcohol copolymer (81/19); vinyl chloride/ vinyl acetate copolymer (83/17 and lower); vinyl pyrrolidone/vinyl acetate/butyl acrylate copolymer (10/78/12 and 10/70/20); vinyl pyrrolidone/vinyl acetate/butyl acrylate/styrene sulfonate copolymer (10/70/17/5); vinyl pyrrolidone/vinyl propionate copolymer (5/95); vinyl caprolactam/vinyl acetate copolymer (5/95); ethyl acrylate/acrylic acid/N-t-butyl acrylamide copolymer; vinyl acetate/crotonic acid copolymer 90/10; vinyl acetate/vinyl propionate/crotonic acid 50/40/10; vinyl acetate/vinyl neodecanoate/ crotonic acid copolymer; and mixtures thereof.

9. The hair conditioner composition of claim 1 wherein the hair styling polymer is present in the composition at a level of from about 2% to about 6%.

10. The hair conditioner composition of claim 9 wherein the hair styling polymer is a vinyl pyrrolidone/vinyl acetate copolymer.

11. The hair conditioner composition of claim 1 wherein the solvent is soluble in water at 25° C. at greater than about 0.5%.

12. The hair conditioner composition of claim 11 wherein the level of solvent is from about 2% to about 6%.

13. The hair conditioner composition of claim 12 wherein the solvent for the hair styling polymer is selected from the group consisting of iso-propanol, butyl alcohol, amyl alcohol, phenyl ethanol, benzyl alcohol, ethyl butyrate, iso-propyl butyrate, phenyl ethyl dimethyl carbinol, and mixtures thereof.

14. The hair conditioner composition of claim 13 wherein the ratio of polymer to solvent is from about 40:60 to about 60:40.

15. The hair conditioner composition of claim 10 wherein the solvent for the hair styling polymer is selected from the group consisting of benzyl alcohol, ethyl butyrate, phenyl ethanol, phenyl ethyl dimethyl carbinol, and mixtures thereof.

16. The hair conditioner composition of claim 1 wherein the hair conditioning agent comprises a cationic surfactant.

17. The hair conditioner composition of claim 16 wherein the hair conditioning agent comprises a quaternary ammonium-containing cationic surfactant material.

18. The hair conditioner composition of claim 17 wherein the hair conditioning agent comprises a dialkyl dimethyl ammonium chloride.

19. The hair conditioner composition of claim 18 wherein the hair conditioning agent comprises a dialkyl dimethyl ammonium chloride selected from the group consisting of ditallowdimethyl ammonium chloride, dicetyl dimethyl ammonium chloride, stearyl dimethyl benzyl ammonium chloride, cetyl trimethyl ammonium chloride and mixtures thereof.

20. The hair conditioner composition of claim 16 wherein the hair conditioning agent is selected from the group consisting of stearylamine hydrochloride, soyamine chloride, stearylamine formate, N-tallowpropane diamine dichloride, stearamidopropyl dimethyl amine citrate, and mixtures thereof.

21. The hair conditioner composition of claim 16 wherein the hair conditioning agent additionally comprises a lipid material.

22. The hair conditioner composition of claim 21 wherein the lipid material is selected from the group consisting of cetyl alcohol, stearyl alcohol, cetyl palmitate, glyceryl monostearate, and mixtures thereof.

23. The hair conditioner composition of claim 1 wherein the hair conditioning agent comprises a silicone conditioning agent, which is present in the conditioner composition as a separate dispersed phase.

24. The hair conditioner composition of claim 23 wherein the silicone conditioning agent is present at a level of from about 0.01% to about 10%.

25. The hair conditioner composition of claim 24 wherein the silicone conditioning agent is present at a level of from about 0.1% to about 5% and comprises a polydimethyl siloxane gum having a viscosity at 25° C. greater than about 1,000,000 centipoise, and a dimethicone fluid having a viscosity at 25° C. of from about 2 centipoise to about 100,000 centipoise, wherein the ratio of gum to fluid is from about 30:70 to about 70:30.

26. The hair conditioner composition of claim 23 wherein the silicone conditioning agent comprises a siloxane macromer grafted to the hair styling polymer.

27. The hair conditioner composition of claim 7 wherein the conditioning agent comprises a siloxane macromer grafted to the hair styling polymer.

28. The hair conditioner composition of claim 27 wherein the hair styling polymer is selected from the group consisting of vinyl pyrrolidone/polydimethyl siloxane/vinyl acetate copolymers.

29. The hair conditioner composition of claim 28 wherein the hair styling polymer comprises a vinyl pyrrolidone/polydimethyl siloxane/vinyl acetate copolymer (5/5/90).

30. The hair conditioner composition of claim 24 which additionally comprises from about 0.3% to about 5.0% of a nonionic cellulose ether having a hydroxyethyl molar substitution of from about 2.3 to about 3.3, and being further substituted with a $C_{16}$ alkyl group at from about 0.50% to about 0.95%, by weight; and from about 0.3% to about 5.0% of a water-soluble polymeric material which is selected from the group consisting of hydroxyethyl cellulose, hydroxypropyl cellulose, hydroxypropylmethyl cellulose, polyethylene glycol, polyacrylamide, polyacrylic acid, polyvinyl alcohol, polyvinyl pyrrolidone, dextran, carboxymethyl cellulose, acacia plant exudate, ghatti plant exudate, tragacanth plant exudate, sodium alginate, propylene glycol alginate, sodium carrageenan, guar gum, locust bean gum, xanthan gum and mixtures thereof.

31. The hair conditioner composition of claim 30 additionally comprising from about 0.05% to about 1.0% of a chelating agent selected from the group consisting of ethyl diamine tetracetic acid and salts thereof, nitrilo triacetic acid and salts thereof, hydroxyethylene diamine triacetic acid and salts thereof, diethylene triamine penta-acetic acid and salts thereof, diethanol glycine and salts thereof, ethanol diglycine and salts thereof, citric acid and salts thereof, and phosphoric acid and salts thereof.

32. The hair conditioner composition of claim 30 wherein from about 0.02% to about 2.5% of the water-soluble polymer is selected from the group consisting of water-soluble polymeric materials having a weight average molecular weight greater than about 1,000,000, and water-soluble polymeric materials having strong ionic character.

33. The hair conditioner composition of claim 32 wherein the water-soluble polymeric material having a weight average molecular weight greater than about 1,000,000, or strong ionic character, is selected from the group consisting of xanthan gum, dextran, carboxymethyl celluloses, plant exudates, seaweed extracts, hydroxyethyl celluloses, and mixtures thereof.

34. The hair conditioner composition of claim 24 which additionally comprises from about 0.1% to about 10.0% of a nonionic cellulose ether having a hydroxyethyl molar substitution of from about 2.2 to about 3.3, and being further substituted with a $C_{16}$ alkyl group at from about 0.50% to about 0.95%, by weight; and from about 0.02% to about 0.3% of a water-soluble surfactant having a weight average molecular weight of less than about 20,000, which is selected from the group consisting of cetyl betaine, ammonium lauryl sulfate, ammonium laureth sulfate, cetyl trimethyl ammonium chloride, and mixtures thereof.

35. The hair conditioner composition of claim 34 additionally comprising from about 0.05% to about 1.0% of a chelating agent selected from the group consisting of ethylene diamine tetracetic acid and salts thereof, nitrilo triacetic acid and salts thereof, hydroxyethylene diamine triacetic acid and salts thereof, diethylene triamine penta-acetic acid and salts thereof, diethanol glycine and salts thereof, ethanol diglycine and salts theroef, citric acid and salts thereof, and phosphoric acid and salts thereof.

36. The hair conditioner composition of claim 34 additionally comprising from about 0.02% to about 2.5% of a distributing aid which is selected from the group consisting of water-soluble polymeric materials having a weight average molecular weight greater than about 1,000,000, and water-soluble polymeric materials having strong ionic character.

37. The hair conditioner composition of claim 36 wherein the distributing aid is selected from the group consisting of xanthan gum, dextran, carboxymethyl celluloses, plant exudates, seaweed extracts, hydroxyethyl celluloses, and mixtures thereof.

38. The hair conditioner composition of claim 24 which additionally comprises from about 0.1% to about 10.0% of a nonionic cellulose ether having a hydroxyethyl molar substitution of from about 2.3 to about 3.3, and being further substituted with a $C_{16}$ alkyl group at from about 0.50% to about 0.95%, by weight; and from about 0.01% to about 10.0% of a water-insoluble surfactant having a weight average molecular weight of less than about 20,000, which is selected from the group consisting of stearamide DEA, cocoamide MEA, dimethyl stearamine oxide, glycerol stearate citrate, dihydrogenated tallow dimethyl ammonium chloride, Poloxamer 181, hydrogenated tallow dimethyl betaine, hyrogenated tallow amide DEA, and mixtures thereof.

39. The hair conditioner composition of claim 38 additionally comprising from about 0.05% to about 1.0% of a chelating agent selected from the group consisting of ethylene diamine tetracetic acid and salts thereof, nitrilo triacetic acid and salts thereof, hydroxyethylene diamine triacetic acid and salts thereof, diethylene triamine penta-acetic acid and salts thereof, diethanol glycine and salts thereof, ethanol diglycine and salts thereof, citric acid and salts thereof, and phosphoric acid and salts thereof.

40. The hair conditioner composition of claim 38 additionally comprising from about 0.02% to about 2.5% of a distributing aid which is selected from the group consisting of water-soluble polymeric materials having a weight average molecular weight greater than about 1,000,000, and water-soluble polymeric materials having strong ionic character.

41. The hair conditioner composition of claim 40 wherein the distributing aid is selected from the group consisting of xanthan gum, dextran, carboxymethyl celluloses, plant exudates, seaweed extracts, hydroxyethyl celluloses, and mixtures thereof.

42. A rinse-off hair conditioner composition comprising:
   a. from about 0.2% to about 3% of a silicone conditioning agent which comprises a polydimethylsiloxane gum having a viscosity at 25° C. greater than about 1,000,000 centipoise and a dimethicone fluid having a viscosity at 25° C. of between about 2 centipoise and about 100,000 centipoise, wherein the ratio of gum to fluid is from about 40:60 to about 60:40;

b. from about 2% to about 6% of a hair styling polymer selected from polyvinyl pyrrolidone/vinyl acetate copolymers, having a weight average molecular weight of from about 10,000 to about 2000,000, a Tg of from about 20° C. to about 60° C., and a solubility parameter, δ, of from about 11 to about 11.5;

c. from about 2% to about 6% of a non-aqueous solvent which will solubilize said polymer selected from the group consisting of benzyl alcohol, ethyl butyrate, phenyl ethanol, phenyl ethyl dimethyl carbinol, and mixtures thereof; and d. the balance, an aqueous carrier;

wherein the polymer and solvent are present in the conditioner composition as a dispersed fluid phase and the ratio of polymer to solvent is from about 40:60 to about 60:40.

43. A rinse-off hair conditioner composition comprising:

a. from about 0.2% to about 3% of a silicone conditioning agent which comprises a polydimethylsiloxane gum having a viscosity at 25° C. greater than about 1,000,000 centipoise and a dimethicone fluid having a viscosity at 25° C. of between about 2 centipoise and about 100,000 centipoise, wherein the ratio of gum to fluid is from about 40:60 to about 60:40;

b. from about 2% to about 6% of a hair styling polymer selected from t-butyl acrylate homopolymers, having a weight average molecular weight of from about 10,000 to about 200,000, a Tg of from about 20° C. to about 60° C.;

c. from about 2% to about 6% of a non-aqueous solvent which will solublize said polymer selected from the group consisting of benzyl alcohol, ethyl butyrate, phenyl ethanol, phenyl ethyl dimethyl carbinol, and mixtures thereof; and d. the balance, an aqueous carrier;

wherein the polymer and solvent are present in the conditioner composition as a dispersed fluid phase, and the ratio of polymer to solvent is from about 40:60 to about 60:40.

44. A rinse-off hair conditioner composition comprising:

a. from about 2% to about 6% of a hair styling and hair conditioning polymer which comprises a polyvinyl pyrrolidone/polydimethyl siloxane/vinyl acetate copolymer, wherein the nonsiloxane backbone of the copolymer has a weight average molecular weight of from about 10,000 to about 200,000, a Tg of from about 20° C. to about 60° C., and a solubility parameter, δ, of from about 11.0 to about 11.5;

b. from about 2% to about 6% of a non-aqueous solvent which will solubilize said polymer selected from the group consisting of benzyl alcohol, ethyl butyrate, phenyl ethanol, phenyl ethyl dimethyl carbinol, and mixtures thereof; and c. the balance, an aqueous carrier;

wherein the polymer and solvent are present in the conditioner composition as a dispersed fluid phase and the ratio of copolymer to solvent is from about 40:60 to about 60:40.

45. A method for providing conditioning and styling hold to hair, said method comprising rinsing the hair with the hair conditioner composition of claim 1.

46. A method for providing conditioning and styling hold to hair, said method comprising rinsing the hair with the hair conditioner composition of claim 42.

47. A method for providing conditioning and styling hold to hair, said method comprising rinsing the hair with the hair conditioner composition of claim 43.

48. A method for providing conditioning and styling hold to hair, said method comprising rinsing the hair with the hair conditioner composition of claim 44.

* * * * *

UNITED STATES PATENT AND TRADEMARK OFFICE
CERTIFICATE OF CORRECTION

PATENT NO. : 5,120,531
DATED : June 9, 1992
INVENTOR(S) : R. L. Wells, B. T. King, M. A. Snyder, D. H. Frey It is certified that error appears in the above-indentified patent and that said Letters Patent is hereby corrected as shown below:

In the title "Hair Styling Conditioners" should read--Hair Styling Conditioners Containing Hair Styling Polymers, with Particular Solubility Parameter, and Particular Non-Aqueous Solvent--

Column 1 in the title "Hair Styling Conditioners" should read--Hair Styling Conditioners Containing Hair Styling Polymers, with Particular Solubility Parameter, and Particular Non-Aqueous Solvent--

Column 13, line 45 "1 to 3°C" should read--- 1 to 3. C ---.

Column 16, line 46 "group is" should read--group" is--

Column 20, line 9 "TiO$_z$" should read--TiO$_2$--

Column 22, line 11 "Silicone Conditioning Agent 5.0" should read-- Silicone Conditioning Agent Premix --

Claim 34, column 25, line 64, "2.2" should read--2.3--

Claim 42, column 27, line 9 "2000,000," should read--200,000,--

Signed and Sealed this

Fourth Day of March, 1997

BRUCE LEHMAN

Attest:

Attesting Officer

Commissioner of Patents and Trademarks